US010053708B2

(12) United States Patent
Ortiz et al.

(10) Patent No.: US 10,053,708 B2
(45) Date of Patent: Aug. 21, 2018

(54) TCR(ALPHA)-LCR-DERIVED GENE REGULATORY CASSETTES

(71) Applicant: Research Foundation of the City University of New York, New York, NY (US)

(72) Inventors: Benjamin D. Ortiz, New York, NY (US); Armin Lahiji, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 15/309,995

(22) PCT Filed: May 11, 2015

(86) PCT No.: PCT/US2015/030166
§ 371 (c)(1),
(2) Date: Nov. 9, 2016

(87) PCT Pub. No.: WO2015/172147
PCT Pub. Date: Nov. 12, 2015

(65) Prior Publication Data
US 2017/0240918 A1 Aug. 24, 2017

Related U.S. Application Data

(60) Provisional application No. 61/990,807, filed on May 9, 2014.

(51) Int. Cl.
*C12N 15/85* (2006.01)
*C07K 14/725* (2006.01)

(52) U.S. Cl.
CPC .......... *C12N 15/85* (2013.01); *C07K 14/7051* (2013.01); *C12N 2740/15043* (2013.01); *C12N 2830/46* (2013.01)

(58) Field of Classification Search
None
See application file for complete search history.

(56) References Cited

FOREIGN PATENT DOCUMENTS

| JP | 2003199587 | 7/2003 |
|---|---|---|
| WO | 1997011191 | 3/1997 |

OTHER PUBLICATIONS

Jenks, Trends in Comparative Endocrinology and Neurobiology, 2009. Ann. N. Y. Acad. Sci. vol. 1163, pp. 17-30.*
Dickmeis, Briefings in Functional Genomics and Proteomics, 2005. vol. 3, No. 4, pp. 332-350.*
Verma et al. (1997, Nature, vol. 389, pp. 239-242).*
Anderson et al.(1998, Nature, vol. 392, pp. 25-30).*
Palu et al.(1999, Journal of Biotechnology, vol. 68, pp. 1-13).*
Poole et al. (Gene, 2001. vol. 269, pp. 1-12).*
Ortiz, B. et al.; A New Element within the T-Cell Receptor alpha Locus Requiredfor Tissue-Specific Locus Control Region Activity; Molecular and Cellular Biology; Mar. 1999; pp. 1901-1909; vol. 19, No. 3; American Society for Microbiology.
Ortiz, B. et al.; Function and Factor Interactions of a Locus Control Region Element in the Mouse T Cell Receptor-alpha/Dad1 Gene Locus1; The Journal of Immunology; Oct. 1, 2001; pp. 3836-3845; 167(7); The American Association of Immunologists.
Harrow, F. et al.; Factors Binding a Non-classical Cis-element Prevent Heterochromatin Effects on Locus Control Region Activity; The Journal of Biological Chemistry; Apr. 23, 2004; pp. 17842-17849; vol. 279, No. 17; The American Society for Biochemistry and Molecular Biology, Inc.
Gosmos-Klein, J. et al; CTCF-Independent, but Not CTCF-Dependent, Elements Significantly Contribute to TCR-alpha Locus Control Region Activity1; The Journal of Immunology; Jul. 15, 2007; pp. 1088-1095.; vol. 179 No. 2 ; The American Association of Immunologists, Inc.
Winoto, A. et al.; A novel, inducible and T cell-specific enhancer located at the 3' end of the T cell receptor alpha locus; The EMBO Journal; 1989; pp. 729-733; vol. 8 No. 3; IRL Press.
Magdinier, F. et al.; Both CTCF-dependent and -independent Insulators Are Found between the Mouse T Cell Receptor alpha and Dad1 Genes; The Journal of Biological Chemistry; Jun. 11, 2004; pp. 25381-25389; vol. 279, No. 24; JBC Papers in Press.
Sleckman, B. et al.; Function of the TCR(alpha) Enhancer in alpha beta and gamma delta T Cells; Immunity; Oct. 1997; pp. 505-515; vol. 7; Cell Press.
Ortiz, B. et al.; Adjacent DNA elements dominantly restrict the ubiquitous activity of a novel chromatin-opening region to specific tissues; The EMBO Journal; 1997; pp. 5037-5045; vol. 16, No. 16; Oxford University Press.
Lahiji, A. et al.; Activity in T Cells Derived In Vitro from Complete TCR-alpha Gene Locus Control Region Activity in T Cells Derived In Vitro from Embryonic Stem Cells; The Journal of Immunology; May 29, 2013; pp. 472-479; vol. 191; The American Association of Immunologists, Inc.
Tasher, D. et al.; The genetic basis of severe combined immunodeficiency and its variants; The Application of Clinical Genetics; Aug. 6, 2012; pp. 67-80; Dovepress.
Fedorov, V et al.; PD-1- and CTLA-4-Based Inhibitory Chimeric Antigen Receptors (iCARs) Divert Off-Target Immunotherapy Responses; Sci Transl Med; Dec. 11, 2013; pp. 1-12; vol. 5 Issue 215.
Kloss, C. et al.; Combinatorial antigen recognition with balanced signaling promotes selective tumor eradication by engineered T cells; nature biotechnology; Dec. 16, 2012; pp. 71-76; vol. 31 No. 1; Nature America Inc.
Tebas, P. et al; Gene Editing of CCR5 in Autologous CD4 T Cells of Persons Infected with HIV; The New England Journal of Medicine; Mar. 6, 2014; pp. 901-910; vol. 370 No. 10; The New England Journal of Medicine.
Tebas, P. et al; Antiviral effects of autologous CD4 T cells genetically modified with a conditionally replicating lentiviral vector expressing long antisense to HIV; Blood; Feb. 28, 2013; pp. 1524-1533; vol. 121, No. 9.

(Continued)

*Primary Examiner* — Celine Qian
(74) *Attorney, Agent, or Firm* — Peter J. Mikesell; Schmeiser, Olsen & Watts LLP

(57) ABSTRACT

A method of delivering a transgene to a cell is provided. The method uses a vector that contains a T-cell receptor alpha locus control region (TCRαLCR) derived gene regulatory cassette having fewer than 5.0-kb. The method delivers the transgene with spatiotemporally specific gene expression and silencing-prevention controls to a cell such that a predetermined subset of progeny cell-types express a gene product from the transgene. Other progeny of the cell diminish, or silence, the expression of the gene product.

15 Claims, 11 Drawing Sheets

(56) References Cited

OTHER PUBLICATIONS

Porter, D. et al.; Chimeric Antigen Receptor—Modified T Cells in Chronic Lymphoid Leukemia; The New England Journal of Medicine; Aug. 25, 2011; pp. 725-733; vol. 365 No. 8; The New England Journal of Medicine.

Santoso, B. et al.; Control of Organ-specific Demethylation by an Element of the T-Cell Receptor-alpha Locus Control Region; The Journal of Biological Chemistry; Jan. 21, 2000; pp. 1952-1958; vol. 275, No. 3; The American Society for Biochemistry and Molecular Biology, Inc.

ISA/US; International Search Report/Written Opinion for International Application PCT/US2015/030166 dated Oct. 1, 2015.

Kowolik, C. et al.; Locus Control Region of the Human CD2 Gene in a Lentivirus Vector Confers Position-Independent Transgene Expression; Journal of Virology, May 2001; pp. 4641-4648; vol. 75, No. 10; American Society for Microbiology.

Ellis, J. et al.; A dominant chromatin-opening activity in 5' hypersensitive site 3 of the human beta-globin locus control region; The EMBO Journal; 1996; pp. 562-568; vol. 15, No. 3; Oxford University Press.

Zhumabekov et al.; Improved version of a human CD2 minigene based vector for T cell-specific expression in transgenic mice; Journal of Immunological Methods; Sep. 1995; pp. 133-140; vol. 185, Issue 1; Elsevier.

May, C. et al.; Therapeutic haemoglobin synthesis in beta-thalassaemic mice expressing lentivirus-encoded human beta-globin; Letters to Nature; Jul. 6, 2000; pp. 82-86; vol. 406; Macmillan Magazines Ltd.

Skarnes, W. et al.; A conditional knockout resource for the genome—wide study of mouse gene function; Nature; Jun. 15, 2011; pp. 337-342; 474(7351) doi: 10.1038/nature10163.

Lahiji, A. et al.; Adapting in vitro embryonic stem cell differentiation to the study of Locus Control Regions; J Immunol Methods; Mar. 26, 2014; pp. 135-145; vol. 407; Elsevier B.V.

EMBL Database.; Sequence listing Version AF000941.1 for "Mus musculus DNAse I hypersensitive sites 2-6 of locus control region (LCR) for T-cell receptor alpha chain (TCRa) gene"; GenBank; Feb. 24, 1998; pp. 1-4.

EMBL Database.; Sequence listing ID No. JN960746 for "A conditional knockout resource for the genome—wide study of mouse gene function" Oct. 28, 2011; pp. 1-31.

European Patent Office; Supplementary European Search Report dated Oct. 11, 2017 for European patent application 15789568.1; pp. 1-16.

* cited by examiner

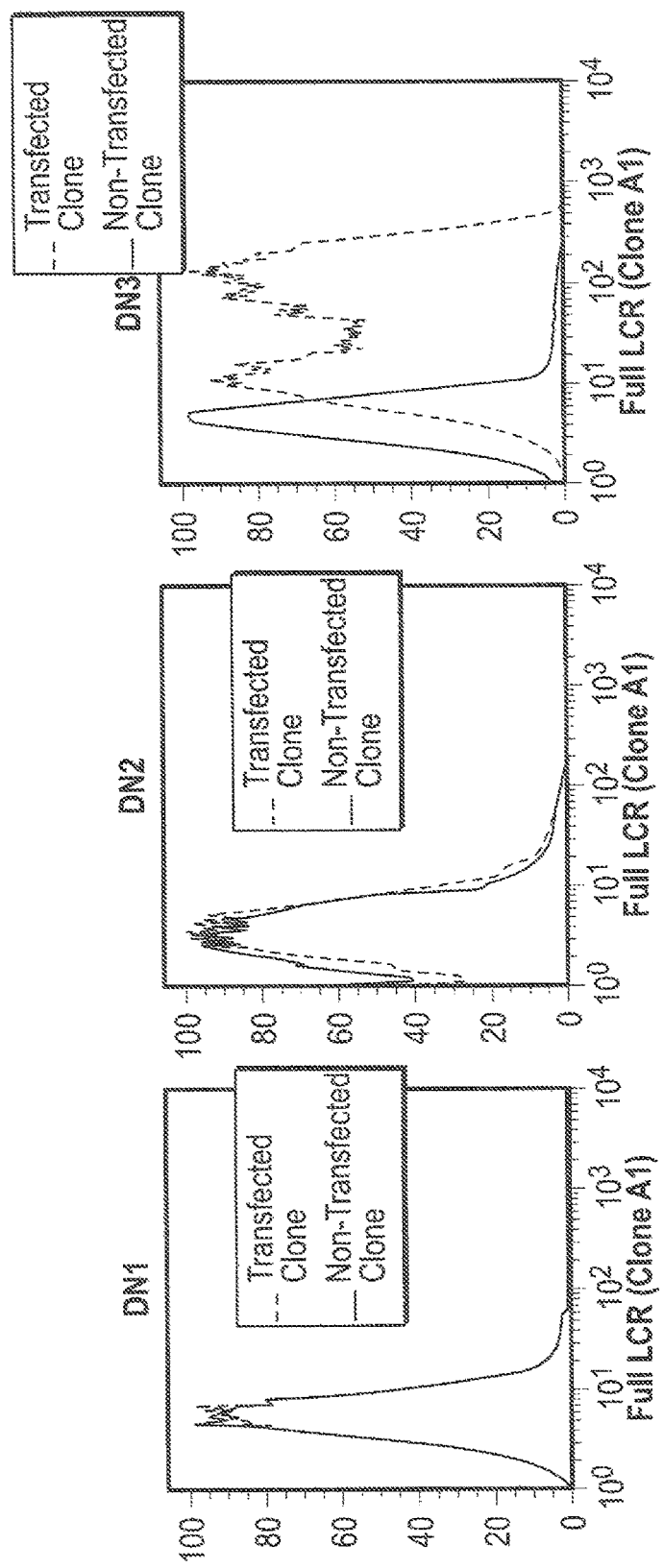

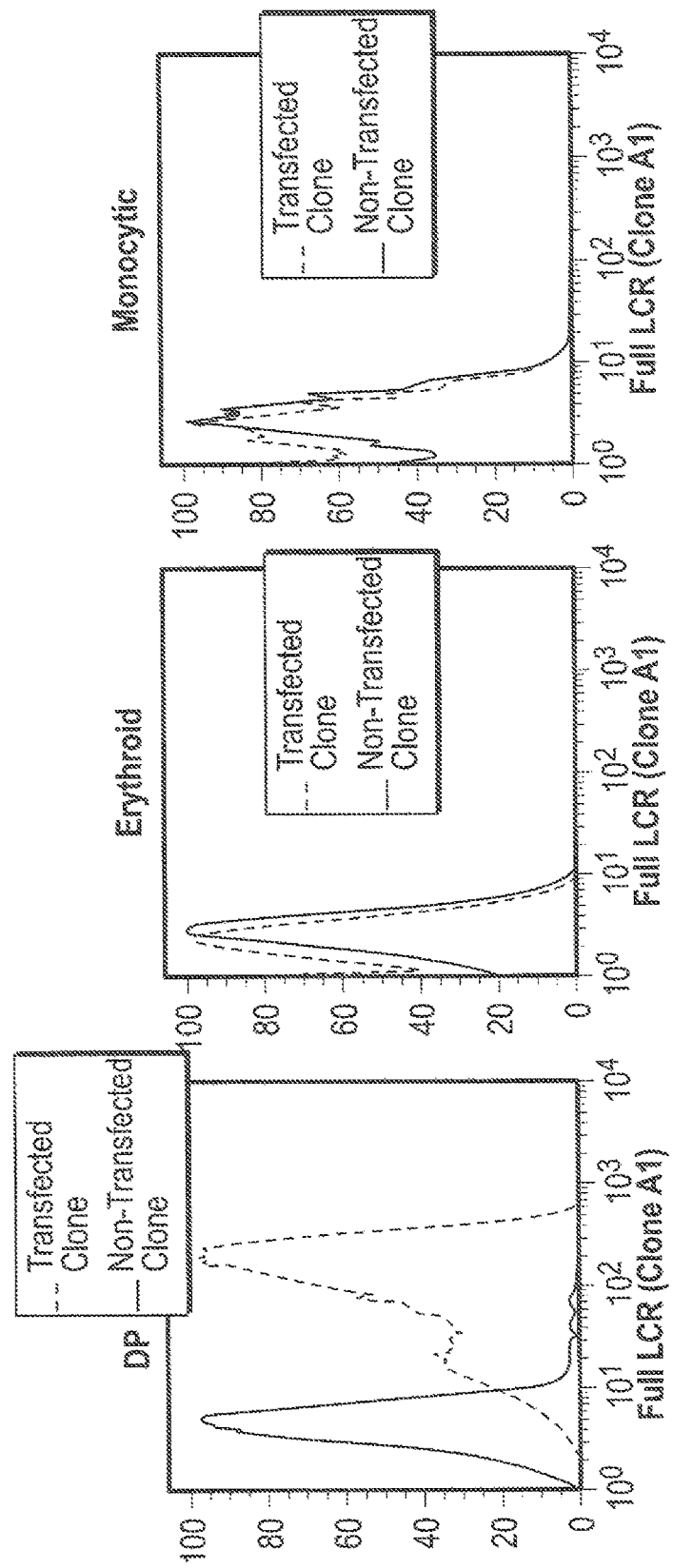

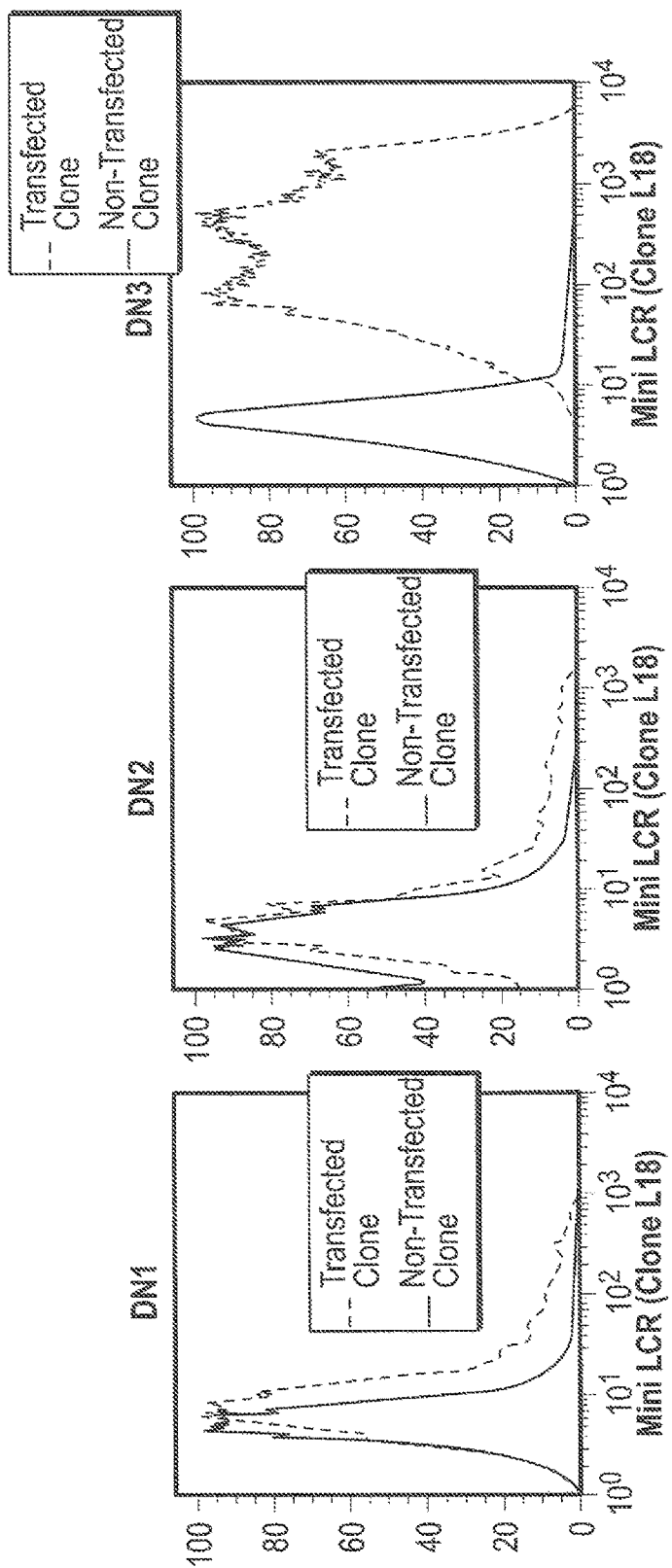

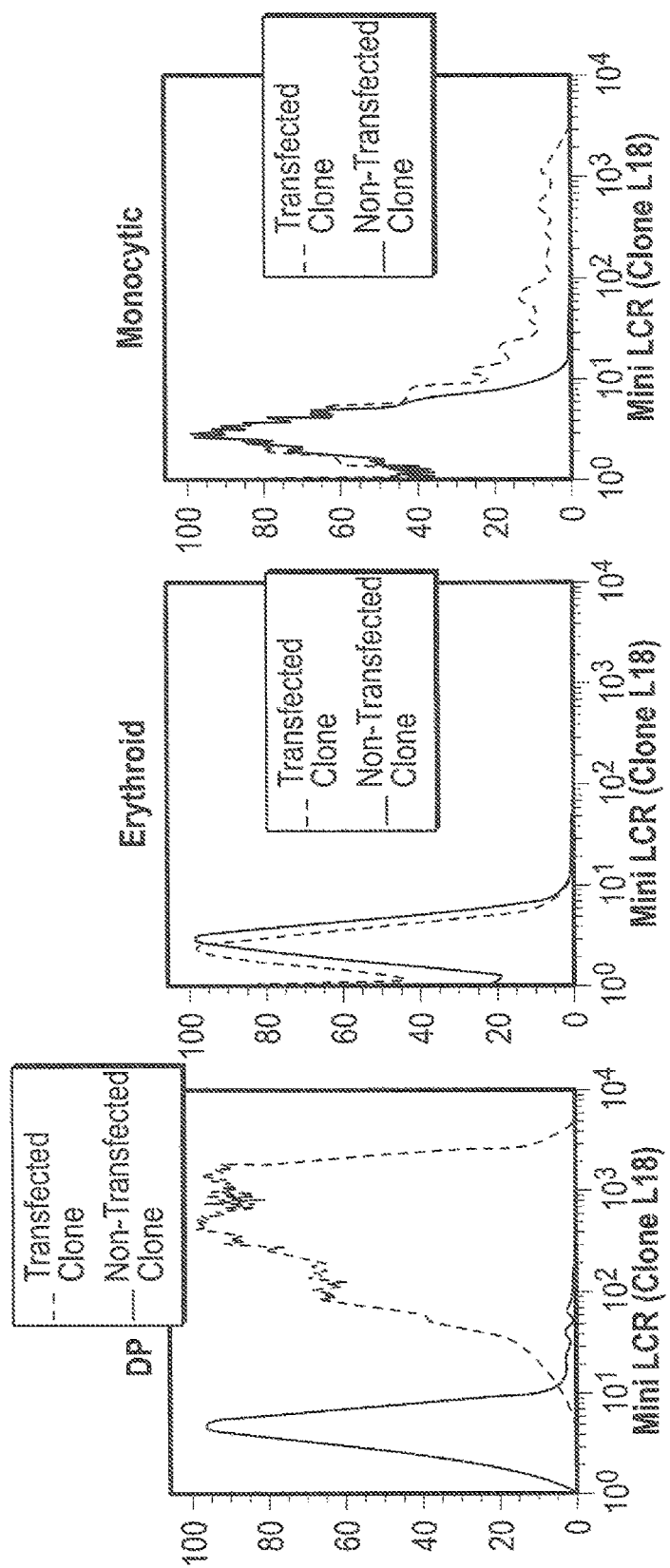

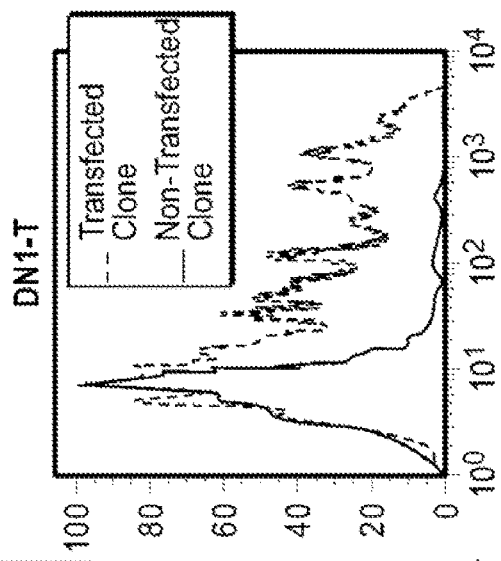
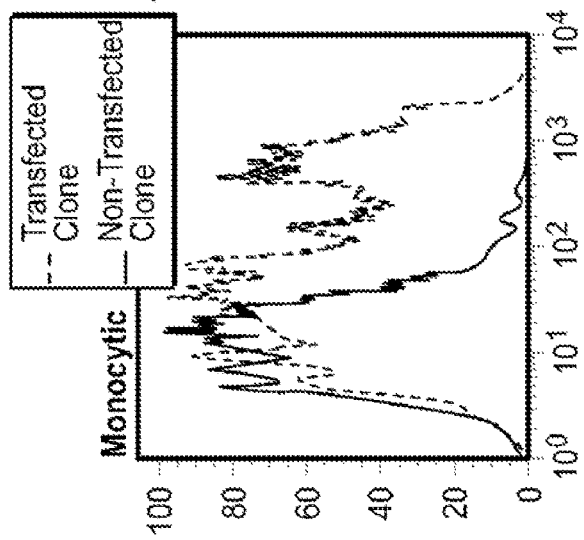
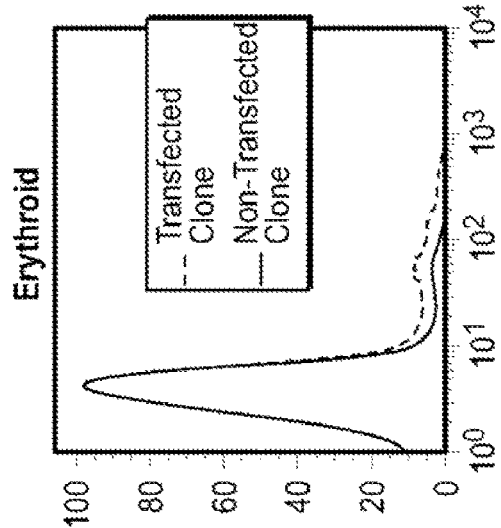

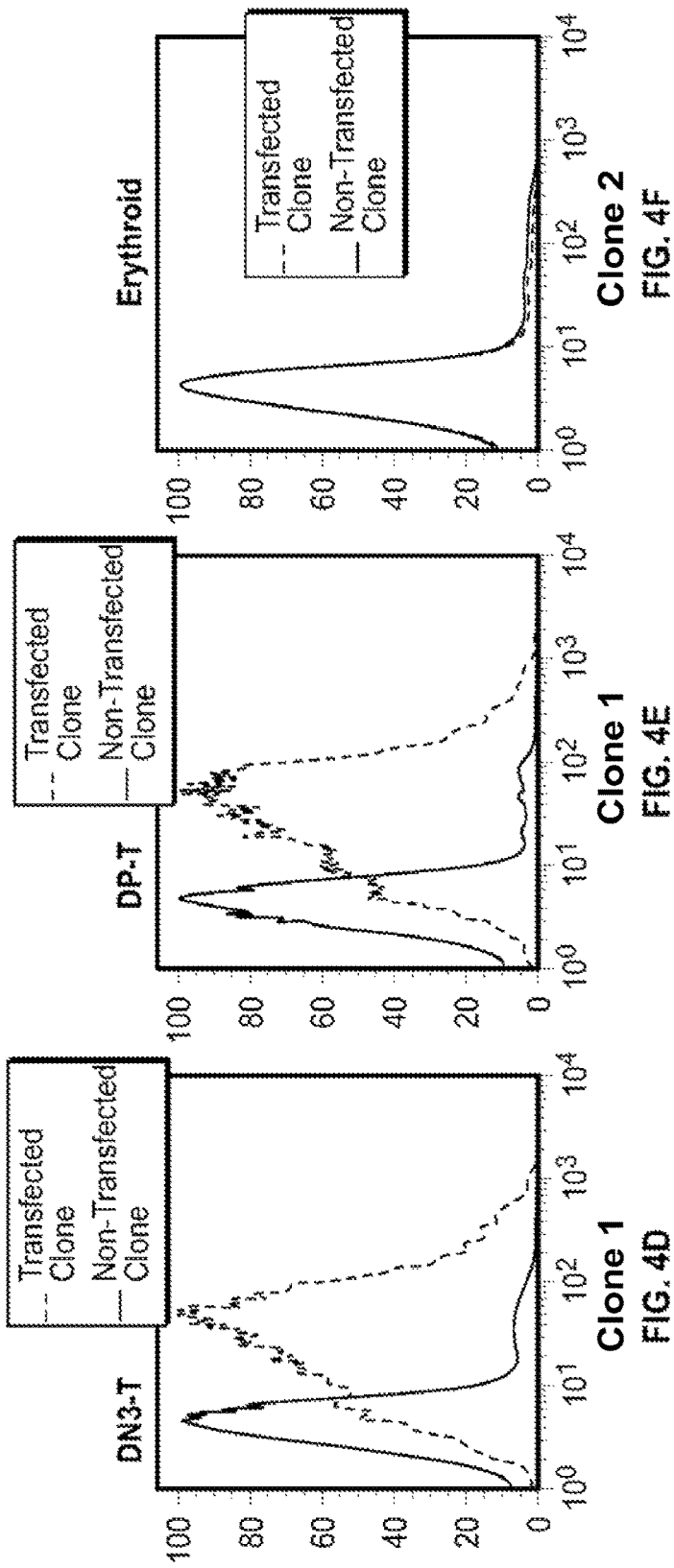

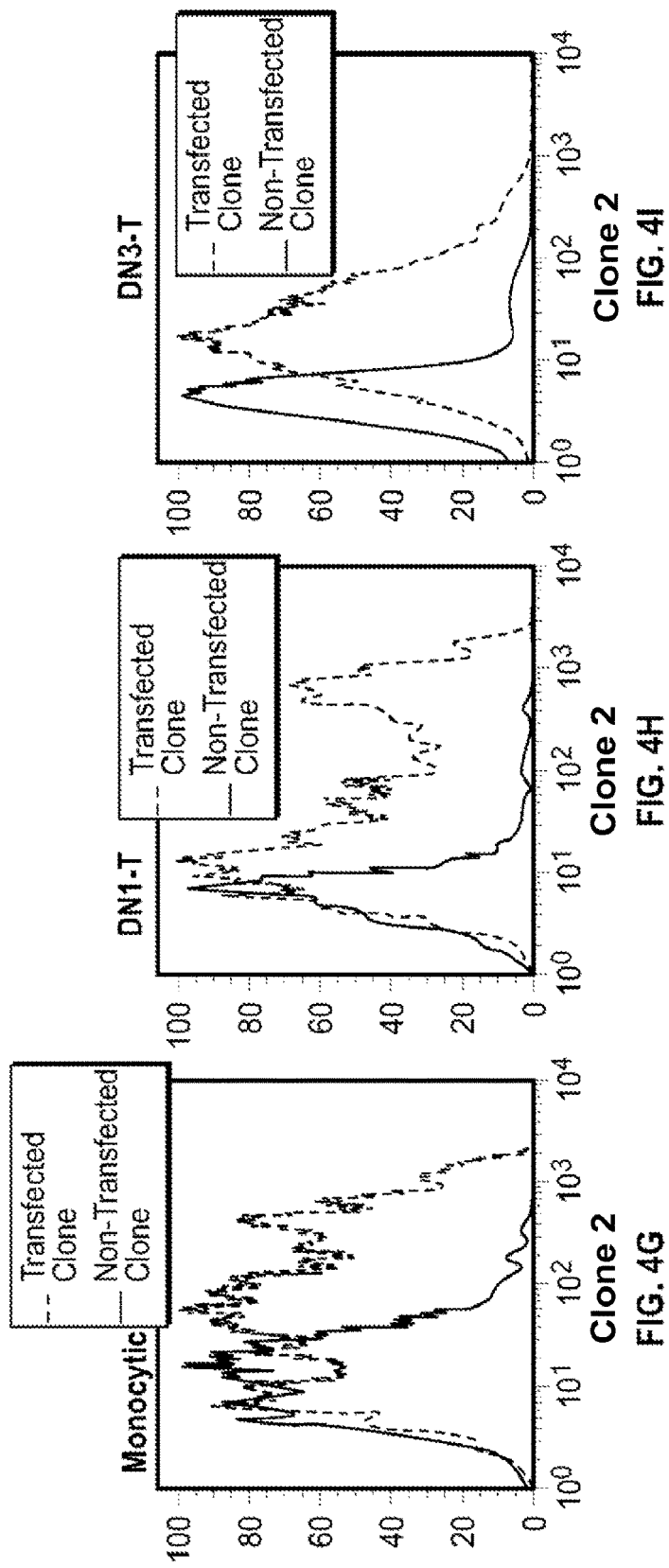

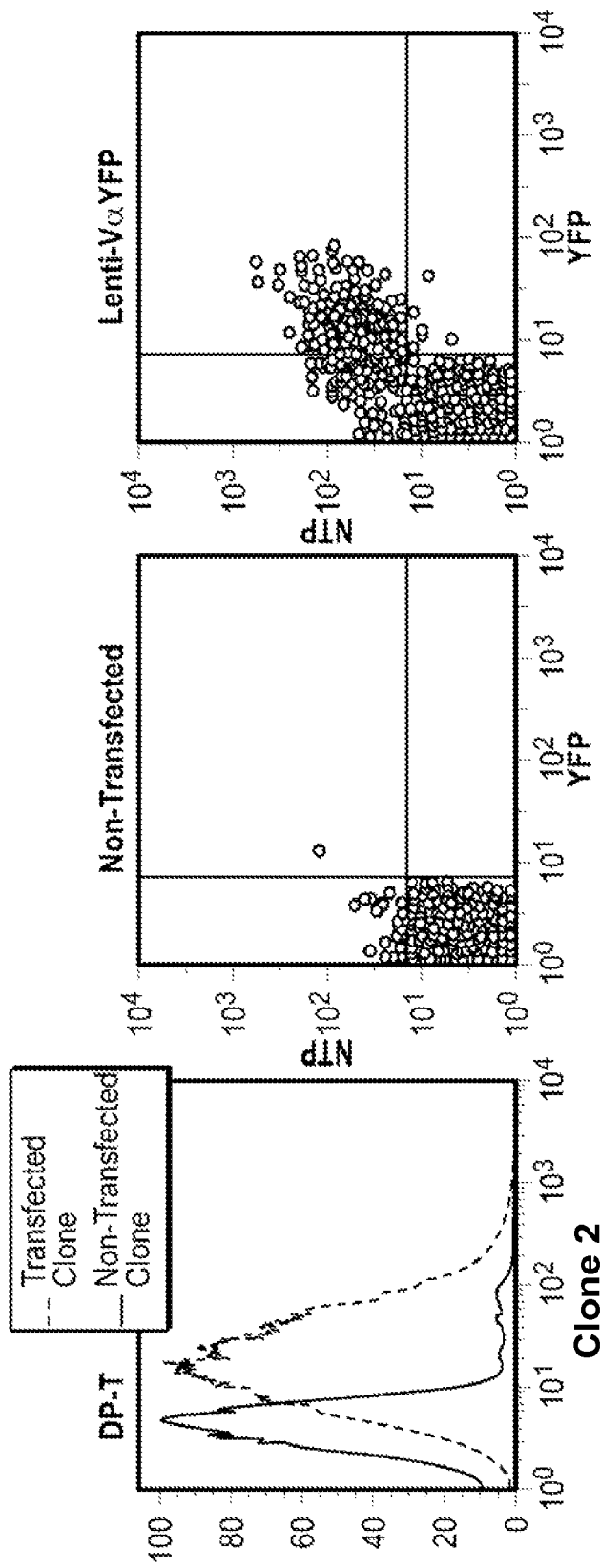

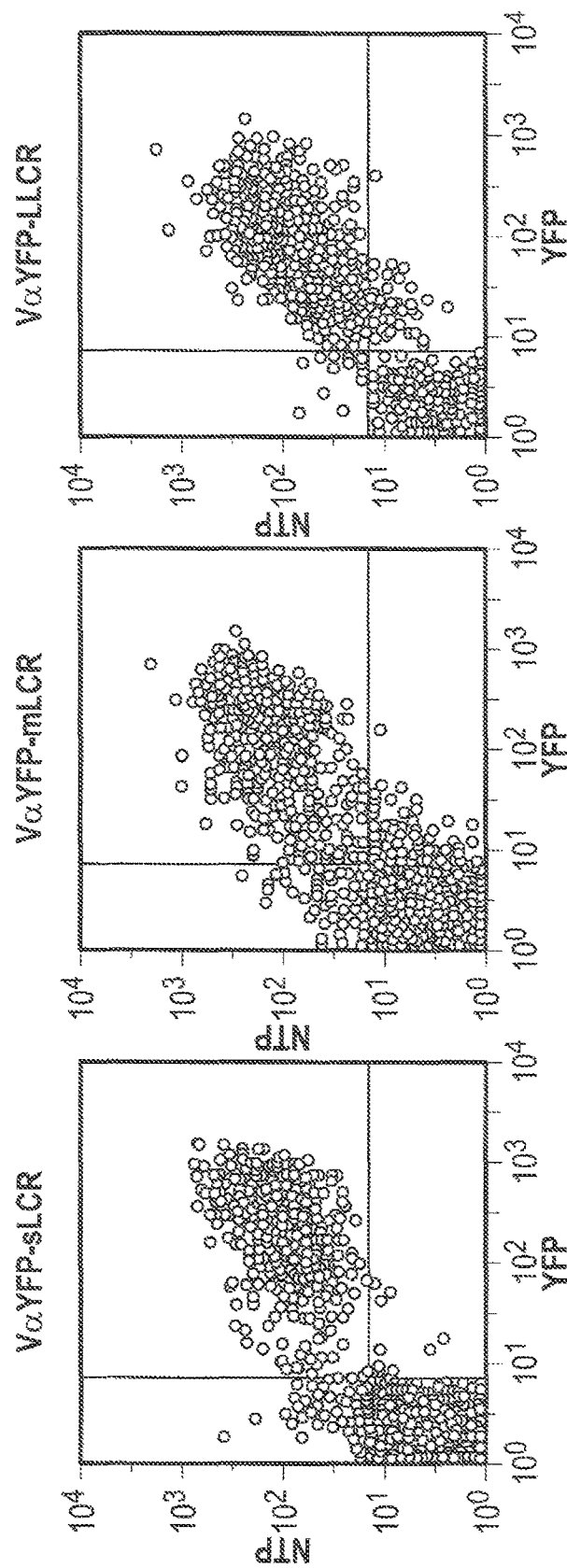

TCR(ALPHA)-LCR-DERIVED GENE REGULATORY CASSETTES

CROSS-REFERENCE TO RELATED APPLICATIONS

This application claims priority to and is a non-provisional of U.S. Patent Application Ser. No. 61/990,807 (filed May 9, 2014) the entirety of which, is incorporated herein by reference.

STATEMENT OF FEDERALLY SPONSORED RESEARCH OR DEVELOPMENT

This invention was made with Government support under Contract Number SC1-GM095402 awarded by the National Institute of Health, National Institute of General Medical Sciences.

REFERENCE TO A SEQUENCE LISTING

This application refers to a "Sequence Listing" listed below, which is provided as an electronic document entitled "20150511_Sequence.txt" (12 kb, created on Apr. 27, 2015), which is incorporated herein by reference in its entirety.

BACKGROUND OF THE INVENTION

The subject matter disclosed herein relates to T-cell receptor alpha (TCRα) locus control region (LCR)-derived gene regulatory cassettes. A locus control region (LCR) is defined by an ability to impart position-independent and high-level tissue-specific expression of a linked transgene. The LCR protects the transgene from certain effects that could silence the transgene if it integrates into inactive chromatin.

The T-cell receptor α (TCRα) gene is exclusively expressed in T-lineage cells. Pre-rearranged TCRα transgenes are expressed only T-cell-bearing tissues, such as thymus and spleen, but not in other organs, such as liver and heart. Even within T-cell-bearing tissues, current vectors used in T-cell gene therapy are not immune from silencing effects that halt the expression of the transgene. Nor are these vectors spatiotemporally specific in their production of the therapeutic transgene product. This limits this approach to vector transduction of terminally differentiated T-cells.

It would be advantageous to transduce stem cell populations with such vectors to produce an ever-renewable source of T-cells expressing the therapeutic gene product. But to do this in a safe way, vectors must be designed to direct high-level therapeutic gene expression to T-cells, and not other stem cell progeny. To do this in an effective way, the vector mast also be equipped with regulatory DNA that enables the vector to be resilient to the silencing effects of heterochromatin dynamics during T-cell differentiation from stem cell precursors. Unfortunately, no vectors are currently known that are entirely satisfactory. A new vector is therefore desired.

The discussion above is merely provided for general background information and is not intended to be used as an aid in determining the scope of the claimed subject matter.

BRIEF DESCRIPTION OF THE INVENTION

A method of delivering a transgene to a cell is provided. The method uses a vector that contains a T-cell receptor alpha locus control region (TCRαLCR) derived gene regulatory cassette having fewer than 5.0-kb. The method delivers the transgene with spatiotemporally specific gene expression and silencing-prevention controls to a cell such that a predetermined subset of progeny cell-types express a gene product from the transgene. Other progeny of the cell diminish, or silence, the expression of the gene product. An advantage that may be realized in the practice of some disclosed embodiments of the method is the ability to direct high-level therapeutic transgene expression to T-cells but not to inadvertently impact other stem cell progeny. Another advantage that may be realized in the practice of some disclosed embodiments is the ability to express a transgene in a manner that is resilient to silencing effects.

In a first embodiment, a method of delivering a gene to a cell is provided such that a predetermined subset of progeny of the cell expresses a predetermined gene product with spatiotemporally specificity and resistance to silencing. The method comprises it a vector to a cell. The vector comprises (a) a T-cell receptor alpha locus control region (TCRαLCR) derived gene regulatory cassette having fewer than 5.0-kb, the TCRαLCR derived gene regulatory cassette comprising a sequence that is at least 70% identical with SEQ ID NO: 1, SEQ ID NO: 2 or SEQ ID NO 3; and (b) a first transgene to be expressed.

In a second embodiment, a method of delivering a gene to a T cell is provided such that the T cell expresses a predetermined gene product with resistance to silencing. The method comprises introducing a vector to a T cell. The vector comprises (a) a T-cell receptor alpha locus control region (TCRαLCR) derived gene regulatory cassette having fewer than 5.0-kb, the TCRαLCR derived gene regulatory cassette comprising a sequence that is at least 70% identical with SEQ ID NO: 3; and (b) a first transgene to be expressed.

In a third embodiment, a vector for delivering a gene to a cell is provided such that a predetermined subset of progeny of the cell expresses a predetermined gene product with spatiotemporally specificity and resistance to silencing. The vector comprises (a) a T-cell receptor alpha locus control region (TCRαLCR) derived gene regulatory cassette having fewer than 5.0-kb, the TCRαLCR derived gene regulatory cassette comprising a sequence that is at least 70% identical with SEQ ID NO: 1, SEQ ID NO: 2 or SEQ ID NO: 3; and (b) a first transgene to be expressed.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used, as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the in encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 3A to FIG. 3L are a series of flow cytometry graphs of reporter gene assay tests comparing the activity of the TαLCR4.0 mini LCR (FIGS. 3G, 3H, 3I, 3J) to that of the full LCR (FIGS. 3A, 3B, 3C, 3D) and at the various stages of T cell development, and in non-T cells (FIGS. 3E, 3F, 3K and 3L);

FIG. 4A to FIG. 4I are a series of flow cytometry graphs of reporter gene assay tests of a first clone (FIGS. 4A, 4B, 4C, 4D, 4E) and a second clone (FIGS. 4F, 4G, 4H, 4I and 4J) showing the activity of TαLCR1.3 mini LCR at the various stages of T cell development, including in non T cells (FIGS. 4A, 4B, 4F and 4G); and FIG. 5A to FIG. 5E shows flow cytometry data on bulk transfected T cells carrying the four indicated lentiviral plasmid constructs.

DETAILED DESCRIPTION OF THE INVENTION

Figure 1:
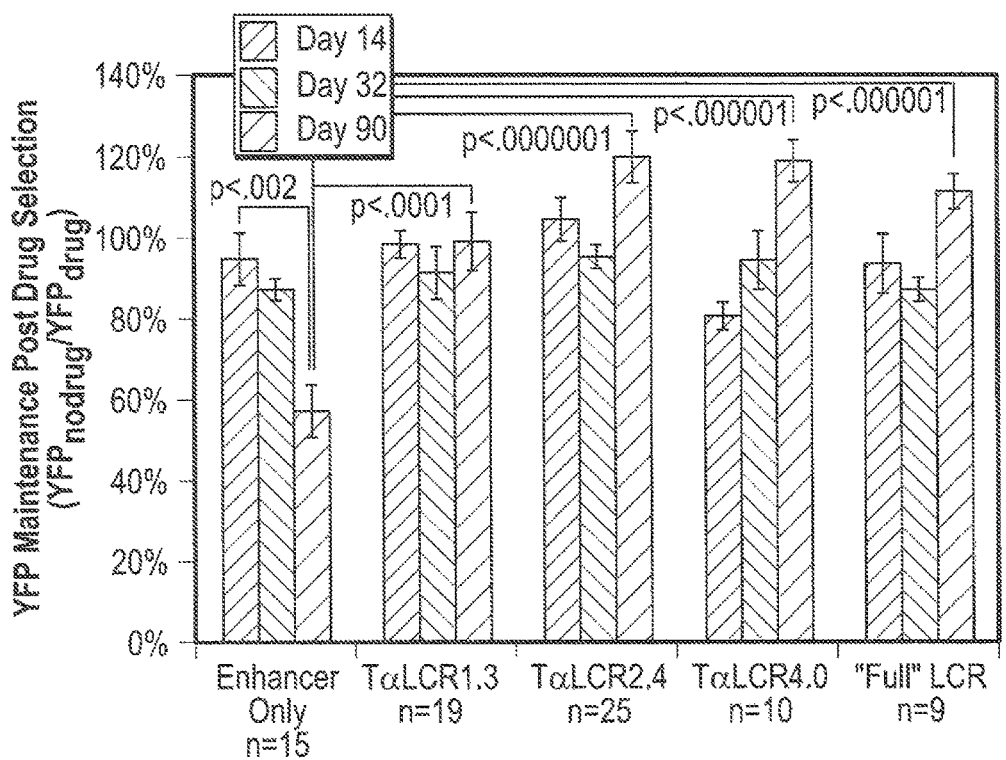
FIG. 1 is a graph depicting yellow fluorescence protein (YFP) maintenance levels in T cells that are stably-transfected with YFP reporter genes linked to one of the following: TCRα enhancer, TαLCR1.3; TαLCR2.4; TαLCR4.0 or the full LCR after 14 days, 32 days and 90 days after withdrawal of drug selection.

Several T-cell receptor alpha (TCRα) locus control region (LCR)-derived gene regulatory cassettes are disclosed herein. Generally, these nucleotides range from 4.0-kbp to 1.3-kbp in DNA length. They contain various combinations of DNA from four functional regions of the TCRαLCR (as defined by studies in transgenic mouse models). These four functional regions refer to specific DNAse I hypersensitive sites (HS) within the TCRαLCR named as follows: HS1, HS1', HS4, HS6. The combinations were made via recombinant DNA technology and were maintained/produced using bacterial plasmid vectors. These regulatory cassettes provide consistent, high-level transgene expression from gene transfer vectors that is: 1) spatiotemporally specific to T-cells and 2) resistant to the silencing effects of genomic heterochromatin spreading. Two cell culture-based assays, were developed to measure these two gene regulatory properties.

Finding the minimal amount of TCRαLCR DNA capable of supporting maximal TCRαLCR activity is desirable for incorporation into viral vectors, which typically have limited space for exogenous DNA sequences. The disclosed SEQ ID NO: 1 provides a robust 4.0-kb mini-LCR (TαLCR4.0) version that is 30% of the original DNA length of the full LCR in the genome (13-kb) but reproduces the qualities of the full-length version. The temporal activation pattern of this 4.0-kb mini-LCR is particularly well suited to driving a pattern of the expression of therapeutic antigen receptors that mimics the natural, physiological expression pattern of endogenous αβ T-cell receptor complex emergence in vivo. The early temporal activation kinetics of the small (1.3-kb) mini-LCR (TαLCR1.3) (SEQ ID NO: 3) is well suited for expressing therapeutic cargo genes to correct inherited, genetic T-cell immunodeficiency, or to express genes in T-cells that confer them with intracellular resistance to infection by T-cell tropic viruses (e.g. HIV). Like TαLCR4.0 and TαLCR1.3, the medium (2.4-kb) mini-LCR (TαLCR2.4) (SEQ ID NO: 2) possesses a strong capacity to insulate linked gene expression from silencing over time m the genuine T cells. A more detailed discussion follows.

Protection from Silencing ("Insulation Capacity")

In pilot experiments (data not shown), data showing that the fall LCR possessed strong insulator-like activity in this assay was obtained, providing 100% protection of inked transgenes from silencing over time in all clones analyzed (n=7 single copy clones). For a description of the full LCR see B. D. Ortiz et al. *Adjacent DNA elements dominantly restrict the ubiquitous activity of a novel chromatin-opening region to specific tissues* The EMBO Journal, Vol. 16 No. 16 (1997) pp. 5037-5045. In the absence of HS1' through HS6 of the LCR sequences, the linked reporter gene experienced gradual silencing over time in all clones analyzed (11-6 single copy clones). Three TCRα-LCR constructions (SEQ ID NO. 1 (TαLCR4.0), SEQ ID NO: 2 (TαLCR2.4) and SEQ ID NO: 3 (TαLCR1.3) were designed to maintain the strong insulator-like activity.

As shown in FIG. 1 three TCRα-derived mini-LCR versions (SEQ ID NO: 1; SEQ ID NO: 2 and SEQ ID NO: 3) can protect a linked transgene from silencing over time in a T-cell culture model. This "insulation capacity" property of these TCRα "mini-LCRs" was tested in a stable transfected DP T-cell line (VL3M2). Transfected VL3-3M2 T-cell clones were generated bearing TCR Vα promoter driven yellow fluorescence (YFP) reporter genes linked to either the TCRα enhancer only, a full LCR cassette (9.5-kb), or the large (SEQ ID NO: 1; TαLCR4.0), medium (SEQ ID NO: 2; TαLCR2.4) or small (SEQ ID NO: 3; TαLCR1.3) mini-LCRs. The TCRα enhancer, which is contained within the HS1 functional region of the LCR, is described in further detail in Winoto and Baltimore, *A novel, inducible and T cell-specific enhancer located at the 3' end of the T cell receptor α locus*, The EMBO Journal, vol. 8, no. 3 (1989) pp 729-33. Specifically, FIG. 1 is a graph of flow cytometry analyses of average % YFP level maintenance (over time) in multiple clones bearing a given reporter construct. "Day" indicates the number of days in the absence of drug selection. The number of clones (n) assessed for each construct is as follows: Enhancer only, n=15, (small, SEQ ID NO: 3), n=19, (medium, SEQ ID NO: 2), n=25 (large, SEQ ID NO: 1), n=10, full LCR, n=9. The depicted p values are calculated using a 2-tailed students T test.

Each done was cultured in duplicate, one under drug selection, the second without drug selection (to permit detection of reporter gene silencing), YFP levels for all cultures were monitored over a 90-day period. The percent YFP maintenance in the absence of drug selection was calculated ($YFP_{nodrug}/YFP_{drug}$) for each done. All three mini-LCR versions were observed to offer substantial protection from reporter gene silencing by this measure. FIG. 1 shows the average % YFP level maintenance over time among the multiple clones containing a given reporter construct. Only the Eα "enhancer only" clones display significant loss of YFP levels in the absence of drug selection. In contrast, all versions of the mini-LCR offer significant protection from reporter gene silencing with activity comparable to that displayed by the full LCR in this assay.

Figure 2A:
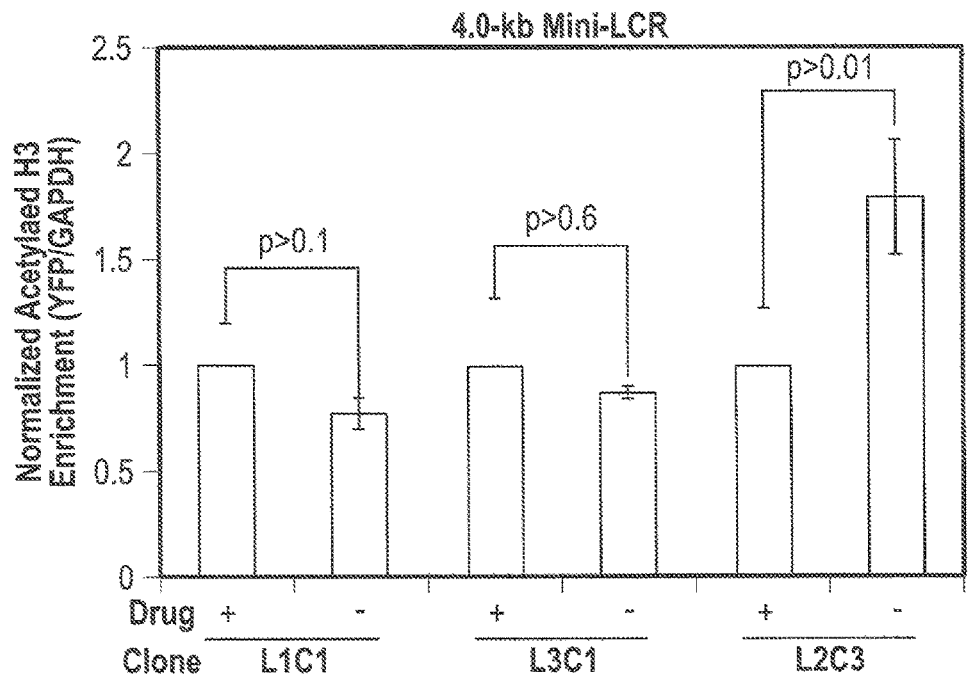
FIG. 2A depicts results of chromatin immuno-precipitation (ChIP) assays of acetylated historic H3 (Millipore 06-599 antibody) at the YFP (VαYFP) reporter gene, while linked to the TαLCR4.0 mini-LCR in stably-transfected T-cell clones in the presence (+) and absence (−) of drug selection.
Figure 2B:
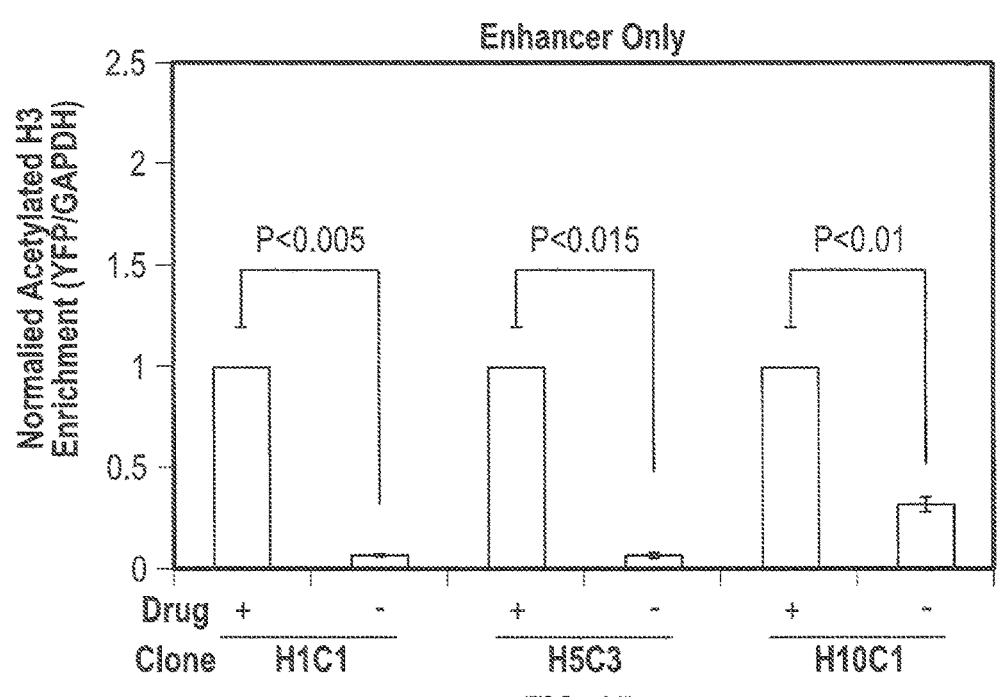
FIG. 2B depicts results of ChIP assays of acetylated histone H3 (Millipore 06-599 antibody) at the YFP (VαYFP) reporter gene while linked to TCRα enhancer only in stably-transfected T-cell clones in the presence (+) and absence (−) of drug selection.

The gradual gene silencing in enhancer-only clones has been linked to changes in historic modifications at the reporter gene locus. Chromatin immuno-precipitation (ChIP) studies show maintenance of euchromatin marks (e.g. diacetylated histone H3) at the reporter locus over time when the TαLCR4.0 (SEQ ID NO. 1) is present (FIG. 2A). Thus, the TαLCR4.0 provides an effective barrier to euchromatin loss and gradual gene silencing over time. As shown in FIG. 2A ChIP assays of acetylated historic H3 (Millipore 06-599 antibody) at the YFP (VαYFP) reporter gene in stably-transfected VL3-3M2 T-cell clones in the presence (+) and absence (−) of drug selection. This mark is maintained in the presence of the TαLCR4.0. In contrast, withdrawal of drug enables detection of acetylated H3 euchromatin loss in the absence of the LCR (FIG. 2B). ChIP signals are quantified by qRT-PCR. VαYFP ChIP signals are normalized to GAPDH (internal control) and expressed as a fraction of the signal seen in the presence of drug selection.

Spatiotemporal Specificity

FIG. 3G to FIG. 3L shows preliminary reporter gene assay tests of the TαLCR4.0 "large mini-LCR" (SEQ ID NO: 1) in various blood cell types derived in vitro from mouse embryonic stem cells (mESC). Full LCR-driven reporter (hCD2) bearing mESC clones (n>12, e.g. A1 see Lahiji, et. al. 2013, J. Immunol 191:472-9) produce erythroid, monocytic and early (DN1 and DN2 stage) T-cell progeny displaying no significant reporter gene activity. In sharp contrast, later stage (DN3 and DP) T-cells robustly express the TCRα LCR-driven reporter gene. Very promisingly, mESC clones bearing the TαLCR4.0-driven reporter gene (n=4, e.g. L18) show very similar activity to that displayed by the full LCR (FIG. 3A to FIG. 3F).

FIG. 3A to FIG. 3F depicts flow cytometry analyses of the full LCR-driven reporter hCD2 transgene activity in the indicated cell subsets (DN1, DN2, DN3, DP, erythroid and monocytic) derived in vitro from transfected ESC clones. A representative full LCR (A1) and TαLCR4.0 (L18) is shown. FIG. 3A to FIG. 3L each depict mean fluorescence intensity (MF1) of per cell FITC-conjugated anti-hCD2 staining as plotted on a logarithmic scale. Relative to full LCR clones, TαLCR4.0 clones (n=4) show only minor "leakage" of reporter expression in monocytic (10-14% cells in positive gate) and DN1 cells (12-18%).

As shown in FIG. 4F to FIG. 4I, preliminary data has also been obtained characterizing the spatiotemporal control characteristics of the TαLCR1.3 (SEQ ID NO: 3). FIG. 4A to FIG. 4I depict mean fluorescence intensity (ME) of per cell FITC-conjugated anti-hCD2 staining as plotted on a logarithmic scale. The small TαLCR1.3 differs from the large TαLCR4.0 (SEQ ID NO: 1) in that it displays activation at an earlier time point in T-cell development (DN1 stage) and also manifests a moderate level of activity in cells of monocytic lineage. The data for the full LCR is shown in FIG. 4A to FIG. 4E. Specifically FIG. 4A to FIG. 4I depicts a flow cytometry analyses of hCD2 reporter activity (x-axis) in the indicated cell subsets derived in vitro from transfected ESC clones.

These mini-LCRs, in the context of lentiviral gene therapy vectors, can provide cargo gene transcription from lentiviral vectors with the requisite resilience and specificity to be used in gene therapy applications in which T-cells expressing a therapeutic gene product in a patient are derived from genetically engineered stem cell transplants.

The TCRαLCR gives consistent, high-level expression beginning in late stage thymic T-cells and mature peripheral T-cells. This late stage timing is particularly suited to expression of exogenous antigen receptors, premature expression of which during T-cell development is known to cause abnormalities in mice. In contrast, the hCD2 LCR gives consistent high-level activity from early thymic T-cell stages on and is also consistently active in B-lineage cells. Thus the TCRαLCR is likely to be more specific in directing therapeutic gene expression to T-cells than the hCD2 LCR. The β-globin LCR is only active in erythroid lineage cells.

In other embodiments, cell lines are created to test agents affecting TCRα gene expression in cell culture. In still other embodiments, transgenic mouse models are created in which it is desired for the introduced gene's expression to be integration site-independent and directed to late stage thymic T cells and mature peripheral T cells.

The efficacy of the disclosed mini-TCRα LCRs in the context of a lend viral construct has been evaluated. A lentiviral gene transfer vector was obtained. A Vα-promoter-driven YFP reporter gene (creating lenti-VαYFP) was cloned into it and further linked this to each of the mini-LCRs.

FIG. 5A to FIG. 5E shows flow cytometry data on bulk transfected C6VLB T cells carrying the tour lentiviral plasmid constructs. The data show that the NTP viral transduction marker and YFP reporter genes are both functional in all constructs, with higher bulk YFP production seen in the presence of the small (s), medium (m) and large (L) mini TCRα-LCRs with little apparent interference with the function of the NTP transduction marker.

In one embodiment, a method of delivering gene product expressed from a genomically integrated vector to a biological cell is provided. The method comprises introducing a genomically integrated vector to a biological cell. The genomically integrated vector comprises (a) a T-cell receptor alpha locus control region (TCRαLCR) derived gene regulatory cassette having fewer than 5.0-kb, the TCRαLCR derived gene regulatory cassette being at least 70% identical with SEQ ID NO: 1, SEQ ID NO: 2 or SEQ ID NO: 3; and (h) a first transgene to be expressed. In another embodiment, the TCRαLCR derived gene regulatory cassette is at least 80% identical with one of the above-referenced sequences. In yet another embodiment, the TCRαLCR derived gene regulatory cassette is at least 90% identical with one of the above-referenced sequences. In another embodiment, the TCRαLCR derived gene regulatory cassette consists essentially of one of the above-referenced sequences.

The term "transgene" refers to a sequence that includes a promotor and a gene that encodes for a predetermined gene product. The first transgene may be, for example, a short promoter-driven cDNA that encodes a gene product with therapeutic impact. For example, a cDNA may be used to produce a protein in T cells that would substitute for one that would have been produced by an endogenous gene that is congenitally non-functional (for examples, see Tasher et al., *The genetic basis of severe combined immunodeficiency and its variants*, Applications of Clinical Genetics, (Aug. 6, 2012) pp 67-80). Alternatively a cDNA encoding a TCR or chimeric antigen receptor directing T cells to target tumor cells may be used (see Porter et al., *Chimeric Antigen Receptor-Modified T Cells in Chronic Lymphoid Leukemia*, The New England Journal of Medicine, V. 365, (2011) pp 725-33). Alternatively, a cDNA encoding a protein or a non-coding RNA (e.g. miRNA product) that inhibits the life cycle oft T-cell tropic virus inside a T cells may be used (for examples, see Tebas et al., *Gene Editing of CCR5 in Autologous CD4 T Cells of Persons Infected with HIV*, The New England Journal of Medicine, vol. 370, no. 10 (Mar. 6, 2014) pp 901-910 and Tebas et al., *Antiviral effects of autologous CD4 T cells genetically modified with a conditionally replicating lentiviral vector expressing long antisense to HIV*, Blood, vol. 121. no. 9, (Feb. 26, 2013), pp 1524-1533). The transgene may be linked 5' or 3' to the TCRαLCR derived gene regulatory cassette.

In one embodiment, a second transgene is also provided. The second transgene may, for example, attenuate or modulate the function of the first transgene. For example a first CAR cDNA can be coupled with a second inhibitory CAR cDNA to divert off-target T cell responses (ref: Federov, et. al. Sci. Transl. Med. 2013 Dec. 11; 5(215):215ra172.). Alternatively, the first and second transgenes may co-express a set of two incomplete but complementary CAR encoding cDNAs to increase target cell specificity by requiring recognition of two antigens to induce a T cell response (Kloss, et. al. 2013. Nat. Biotechnol. 31:71-5). Alternatively, a first CAR/TCR transgene can be co-expressed with a second transgene expressing a "suicide cDNA" (e.g. thymidine kinase) that will enable elimination of therapeutic gene expressing cells upon administration of a specific drug (e.g. acyclovir). In another embodiment, the first and second transgenes provide intracellular resistance to two T cell tropic viruses at once (e.g. HIV and HTLV-1). The first and second transgenes, in some embodiments, flank the TCRαLCR derived gene regulatory cassette.

In one embodiment, the TCRαLCR derived gene regulatory cassette has fewer than 5.0-kb and is at least 90% identical with SEQ ID NO: 1. In another embodiment, the TCRαLCR derived gene regulatory cassette has fewer than 3.0-kb and is at least 90% identical with SEQ ID NO: 2. In yet another embodiment, the TCRαLCR derived gene regulatory cassette has fewer than 2.0-kb and is at least 90% identical with SEQ ID NO: 3.

Three mini-TCRαLCRs (SEQ ID NO: 1; SEQ ID NO: 2 and SEQ ID NO: 3) were constructed from portions of the endogenous mouse TCRαLCR that had been determined to be functional cis-acting gene regulatory elements. These elements were assembled in the pBlueScript SK I (pBSK) cloning vector (Stratagene) as follows.

Construction of the "Small" Mini-LCR (TαLCR1.3) Cassette (SEQ ID NO: 1)

pS-HS11' PvuII/Sca I: The smallest version of the mini TCRαLCR contains segments of the HS1, HS1' and HS6 functional regions of the full LCR. To isolate the HS1 and 1' region, a PCR scheme was developed to amplify an 804-bp fragment spanning from the Pvu II site located at the 5'-border of the Eα transcriptional enhancer located in HS1 to the Sca site (3 border) located in HS1'. This region contains Eα and ends right after the identified CTCF sites within HS1'. The forward primer included an artificial Xho I site on the 5'-end and the reverse primer included an artificial Cla I site on the 3' end. The sequence for the forward primer was: 5'-GACCTGCTCGAGCTGCACCCT-GAAATGGT-3' (SEQ ID NO: 4). The reverse primer sequence was: 5'-CGAGTCATCGATACTGCTGC-CCCGTGTG-3' (SEQ ID NO: 5). The insertion of these two unique restriction enzyme target sites enabled the insertion of the PCR product into the Xho I and Cla I sites of pBSK. This plasmid contained the functional regions of Eα and HS1' and was termed pS-HS11' PvuII/Sac I.

pS-LCR:

To complete the construction of the small LCR, a 554-bp Bcl I to Bgl II fragment of the HS6 region was placed into the BamHI site of psHS11' PvuII/Sca I. Since digestions of DNA with Bcl I and Bgl II leave both ends compatible with ligation into Bam HI sites, the resulting plasmids was analyzed for clones bearing the fragment in the correct natural genomic orientation. This was confirmed by restriction analysis. The correct plasmid was termed pSLCR, containing the TαLCR1.3 cassette.

Construction of the "Medium" Mini-LCR (TαLCR2.4) Cassette pM-LCR:

The medium version of the mini TCRαLCR (TαLCR2.4) has the same regions HS1, HS1' and HS6 as the small LCR with the addition of an 1127-bp region containing the HS4 element. This ApaL I to Dra I region of HS4 was blunted and ligated into a unique EcoR V site within pSLCR in between the HS1/HS1' and HS6 regions in the natural genomic orientation.

Construction of the "Large" Mini-LCR (TαLCR4.0) Cassette pL-HS11' PvuII/BamHI:

To isolate the enhancer (HS1) and complete HS1' region of the TCRαLCR, a PCR primer pair was designed to amplify a 1052-bp genomic fragment spanning from a Pvu II site located at the 5' border of the Eα transcriptional enhancer in HS1 to a Bam HI site located at the 3'-border of HS1'. The forward primer included an artificial Xho I site on the 5' end and reverse primer included an artificial Cla I site on the 3' end. The sequence for the forward primer was: 5'-GACCTGCTCGAGCTGCACCCTGAAATGGT-3' (SEQ ID NO: 4), while the sequence for the reverse primer was: 5'-CGAGTCATCGATACTGCTGCCCCCGTGTGG-3' (SEQ ID NO: 5). The PCR product was digested with Xho I and Cla I and placed in to their corresponding sites in PBSK. Once assembled, this PBSK plasmid contained the complete HS1 and HS1' region and was termed pL-HS11' PvuII/BamH I.

pL-HS11'/L-HS6:

A 1786-bp Mfe I to Ecl36 II fragment containing the complete HS6 region was excised. This fragment was inserted 3' of the HS1/HS1' DNA in pL-HS11' PvuII/BamH I using the EcoR I site and Sma I sites.

pL-LCR:

The 1127-bp ApaL I to Dra I fragment containing the HS4 region was blunted and inserted into the EcoR V site of pL-HS11'/L-HS6 in a position in between the HS1/HS1' and the HS6 DNA to complete pL-LCR containing the (TαLCR4.0) cassette.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of delivering a gene to a cell such that progeny of the cell expresses a predetermined gene product with spatiotemporal specificity and resistance to silencing, the method comprising:
  introducing, in an in vitro environment, a vector to a cell, the vector comprising:
  (a) a T-cell receptor alpha locus control region (TCRaLCR) derived gene regulatory cassette having fewer than 5.0-kb nucleotides, the TCRaLCR derived gene regulatory cassette comprising a sequence that is SEQ. ID NO: 1 and
  (b) a first transgene to be expressed.

2. The method as recited in claim 1, wherein the cell is a stem cell.

3. The method as recited in claim 1, wherein the cell is a multi-potent precursor cell.

4. The method as recited in claim 3, further comprising permitting the multi-potent precursor cell to proliferate and differentiate to form a population of T-cells and a population of non-T-cell progeny cells, wherein the population of T-cells differentiating from the multi-potent precursor cell expresses the first transgene with a first degree of expression and the population of non-T-cell progeny cells expresses the first transgene with a second degree of expression that is lower than the first degree of expression.

5. The method as recited in claim 4, wherein the second degree of expression is zero.

6. The method as recited in claim 1, wherein the first transgene is directly linked 5' to the TCRαLCR derived gene regulatory cassette.

7. The method as recited in claim 1, wherein the first transgene is directly linked 3' to the TCRαLCR derived gene regulatory cassette.

8. The method as recited in claim 1, wherein the first transgene is promoter-driven cDNA.

9. The method as recited in claim 1, wherein the vector further comprises a second transgene, wherein first transgene and the second transgene flank the T-cell receptor alpha locus control region (TCRαLCR) derived gene regulatory cassette.

10. The method as recited in claim 1, wherein the vector further comprises a second transgene and the second transgene is a promoter-driven cDNA.

11. The method as recited in claim 1, wherein the vector consists of the T-cell receptor alpha locus control region (TCRaLCR) derived gene regulatory cassette and the first transgene.

12. The method as recited in claim 1, wherein the vector consists of the T-cell receptor alpha locus control region (TCRaLCR) derived gene regulatory cassette and the first transgene and a second transgene.

13. A vector for delivering a gene to a cell such that progeny of the cell expresses a predetermined gene product with spatiotemporal specificity and resistance to silencing, the vector comprising:
  (a) a T-cell receptor alpha locus control region (TCRaLCR) derived gene regulatory cassette having fewer than 5.0-kb nucleotides, the TCRaLCR derived gene regulatory cassette comprising, a sequence that is SEQ ID NO: 1 and
  (b) a first transgene to be expressed.

14. The vector as recited in claim 13, wherein the vector further comprises a second transgene, wherein first transgene and the second transgene flank the T-cell receptor alpha locus control region (TCRαLCR) derived gene regulatory cassette.

15. The vector as recited in claim 13, wherein the vector further comprises a second transgene and the second transgene is a promoter-driven cDNA.

* * * * *

UNITED STATES PATENT AND TRADEMARK OFFICE
CERTIFICATE OF CORRECTION

PATENT NO. : 10,053,708 B2
APPLICATION NO. : 15/309995
DATED : August 21, 2018
INVENTOR(S) : Benjamin D. Ortiz and Armin Lahiji Page 1 of 1

It is certified that error appears in the above-identified patent and that said Letters Patent is hereby corrected as shown below:

In the Claims

In Column 17;
At Line 27 that portion of Claim 1 reading "(TCRaLCR)" should read --(TCRαLCR)--;
At Line 28 that portion of Claim 1 reading "TCRaLCR" should read --TCRαLCR--.

In Column 18;
At Line 29 that portion of Claim 11 reading "(TCRaLCR)" should read --(TCRαLCR)--;
At Line 33 that portion of Claim 12 reading "(TCRaLCR)" should read --(TCRαLCR)--;
At Line 40 that portion of Claim 13 reading "(TCRaLCR)" should read --(TCRαLCR)--;
At Line 41 that portion of Claim 13 reading "TCRaLCR" should read --TCRαLCR--.

Signed and Sealed this
Twenty-fifth Day of September, 2018

Andrei Iancu
*Director of the United States Patent and Trademark Office*

SEQUENCE LISTING

<160> NUMBER OF SEQ ID NOS: 5

<210> SEQ ID NO 1
<211> LENGTH: 4120
<212> TYPE: DNA
<213> ORGANISM: Artificial Sequence
<220> FEATURE:
<223> OTHER INFORMATION: Entirely synthetic DNA sequence formed by
standard recombinant DNA technology from four functional regions
of TCR(alpha) LCR.
<220> FEATURE:
<221> NAME/KEY: misc_feature
<222> LOCATION: (803)..(803)
<223> OTHER INFORMATION: n is a, c, g, or t

<400> SEQUENCE: 1

```
gcggccgctc tagaactagt ggatccccccc tctgtgtctc tcaccagcag taagtttgcc      60
atatatgggg aacagccctg tcgtgttccc ctgaagctga ttaccaaatg acccgtgctc     120
cagaagccct cccataggac tgcacgctgc cataggctga ggaatcacgc ttctgttgcc     180
cgggtcacac tggatcaaat cagtctcggg tgtagctgac tacccctatc ctggatgatt     240
gaggcttgcc cattcagtgg gtagtcggcc attagtggta ctggccactg ttggagctgt     300
ggaaaaggag actcccaggc cttaccccca agcgacagaa gcaaagcttt gcattttaac     360
acggtgccag gtggtggtgt gcacccggaa gtctgagatg cccgcatttc cagctctggg     420
tgtatcctgc aactacccgg aagcttaaca gagcttgagc ctctccattc tttattagct     480
ctttgcttag ctagacatac tccagagtga gttaacaagc ctttaggaa tggttgggtt     540
caatataatg acaaaacctg gcaggggtcc tgtgggccaa ggcctagcac tgaggagaag     600
ttcactagga tggctgagcg atcagtgtgc tcgacactcg tgcagacatc ctgcagcttt     660
ccccggagaa gtggatgagg tttactttgg attcaataag cagatatttc agatatgaaa     720
agcaatcgga ctttaagagc aaaggaagac gtcacaacag tacgcgtgaa gatttacatt     780
tctcgcagtg gcttagagcc acntgggccg gtactagtt tccaggcgca gatctgcttt     840
tgtctcgggg ttgtgatttt ccccttggac tagccttggc ggcaggcgta gcttgttgtg     900
agtttgtacc gtttacaaca gtacaaacta ctttcagggg tcttgagttc aaatttgaaa     960
atgcaccata ggcttgctgt agactttagt tagcttgctc tgtggctctc agttccatac    1020
gcacagagag gctaaccgtg ggttattcct caactaggga agggccttcc acaaggctcc    1080
ccgggcggag gggttggttt tgctgactca ggtactgtat gggctgaggg atggatgtcc    1140
tgctgtttcc tgcagcttcc agctcacacc tcctctgtgt gtgtgtgtgg ggggggggt    1200
tattttattt tcctgtgttc aatctgtggg gctgcaagcc atttaccaca actactgtac    1260
attgttcctt gctcggcagt ggtgggaaac agccctttgc accctctgcc tacacacttc    1320
ctgtcgccac ggcatgcaaa tgttcctcct gcttcctctc ccggcagcct gcacctctgc    1380
tcttgatcac gtctgtgatc ttggcccaca aagcggtctt gttacattgt tggaacatac    1440
ttgggaagtg acagagattg ttcccttctt tgggaaagtc agcaagccag ccagcatcag    1500
ctagtttcca gcacctggaa gctactagct cagttgtagt tctggtgggt tgtggactgg    1560
aagtctaggc tagtgtttgg gtgcctcatg acttaagatt tatcttaggg ttttcattgc    1620
tgtgataaaa cgccatgggg tggggtgggg ggtgaagcc catgggagga aagggtttgt    1680
ttcagtttac agctgaaatc catcagtcgg ggaagtcggg gcaggaatgc aaggcaggag    1740
ctgatgctca aaccaggggt gaaagctgcc tgctgcctta gaataccttg ctcagcctgc    1800
tttcttatag ctgggccagc ttgctcaggg aggcaccacc tacatgggtt gggcttccct    1860
```

```
catcagttac aagaaaatgc ccccacaggc ttgccatcaa ctttgagggg acttttttcaa      1920 ttcgataaaa aattaaatat tgccgggcgt ggtccaccct ttattcccag cactcgggag      1980
gaacagaggc aggcggattt ctgagttcga ggccagcctg gtctacagag tgagtttcag      2040
gcatccaggg ctacacagag aaaccctgcc tggaaaaaaa aaaagaaaag aaaaattatg      2100
tcatttccct ttcacctcct tctccctctc atctacttcc tcctccaata ccctcccaat      2160
actttctcaa attcatggcc tctggtttta attgtgatag gtgtgtgtat gtttatgcac      2220
acacacacac acacacacac acacacacac acacacactt atgatttcag agctgaccat      2280
ctggtgttgg atagctggtt gggggcttct ccctggggaa gaatgtttcc cactgtcagt      2340
gttgcttggc tgctgcgctc cttgtttagg gttggagaat ccccccctcac atttctaaga      2400 ccaatctcag agcacacttc ctgtttctct ggttcttaca gtcgttgtgc ccccaacccc      2460
cttctaagat gttccctgcg cctcgggtgc aggagctggg ttgtcgatag atccgctgga      2520
gccgggcacc ccaggatcca cggtcctctg cctctgacag ggtgtggttt tctttctgta      2580
tgcgtgcgtg cgcgtttgtg agtgtgtcag aggacatctt ggcaggagtc ggttctttcc      2640
ttgtaccatg taggtactaa ggttcaagct tgggtcacca gggcgtcact aggtgccttg      2700
tatacagagt catcttgtct tctgattttg ccttatcact gaacttctga ccacggggct      2760
ggcaaggtgg ctcagagagt aaaaacccct tctgagcagc cccggtgatc tgagattgac      2820
cccccccccc agcttccacg cagaggtaga gaactgacta ttgaagttct ctgaccgtca      2880
caggcacgcg ccacaccatc cccgccatga gactgagcct acagtttatg catctattat      2940
gctatgtatt ccctcagcag gggagccctg tccacccatg ctccctggag tggacagggc      3000
tcgggtttgc cattctaatt cagtcctaaa gaggaaccaa gtaagtgatc aagcttatcg      3060
atctgggcct gcgggccata ttccatctcc tggcttccaa cagggtagtt tctttctggg      3120
tttctcttgt agctaggtct cctaaacctg ggtaggcagt gccctgctg cctgaaggcc      3180 tgaccctaga ctcttttgcag gcagagagga tcacacaagt ctggagtcca gtgactggca      3240
cagggcagga ccctgtgaaa cagaagccac ttgtcatttt attttccttt ggaaagagtt      3300
tttccgtagg atgcagggat tttctttatc ccgaataaac acgccgaggg agaaagcctt      3360
ttggtggagt actgctgccc ccgtgtggct accttaagac actacaacag agtgggactc      3420
ccaagacgaa agttttttcag gtttcaggtt ctgcgacttc ctaggaccct gagagacaga      3480
tgtccactag ggttatctct tgacacttaa atttcctcct ggagtggaaa tgagagcgaa      3540
tggggcttct tgtggaaggt atctgttggg gaacgagcct tagctgtgtg tgtaggcagc      3600
tgcctctttc acaacctgtc cagcacaagc tggactggac atagactttc tcccttgaac      3660
taagtatata gacttgtcta atttgagggc aatagaggtc aggggagggg gacttcttgg      3720
gagtggagcc gcagtgcctc cccagccggc tgctgtgaat gggtgttacc accaagacct      3780
gcaagcccca cccaatgtgc tctccgtggc cttcttttct gcacctgtgg ttgggctgcg      3840
gtgtaacggc ccagcctacc tcttctgggc acgtggcccg gagagatctt atctctaact      3900
ctgtattttt aactcctctt tccagaggat gtggcttctg cgggagagct tcaaaggggg      3960
acctgtttgc ccatgtcagc agccgtgacg tcatggaagt gggaggctgt tcagacccaa      4020
acacctggag ggaagtggga aactttttcc atttcctgtt ctacttctgg ctattgattc      4080
actatctgac cagcttaccc atttcagggt gcagctcgag                           4120
```

<210> SEQ ID NO 2

<211> LENGTH: 2483
<212> TYPE: DNA
<213> ORGANISM: Artificial Sequence
<220> FEATURE:
<223> OTHER INFORMATION: Entirely synthetic DNA sequence formed by
      standard recombinant DNA technology from four functional regions
      of TCR(alpha) LCR.

<400> SEQUENCE: 2

| | | | | | |
|---|---|---|---|---|---|
| gcggccgctc | tagaactagt | gtgcttttgt | ctcggggttg | tgattttccc | cttggactag | 60 |
| ccttggcggc | aggcgtagct | tgttgtgagt | ttgtaccgtt | tacaacagta | caaactactt | 120 |
| tcagggtct | tgagttcaaa | tttgaaaatg | caccataggc | ttgctgtaga | ctttagttag | 180 |
| cttgctctgt | ggctctcagt | tccatacgca | cagagaggct | aaccgtgggt | tattcctcaa | 240 |
| ctagggaagg | ccttccaca | aggctccccg | ggcggagggg | ttggttttgc | tgactcaggt | 300 |
| actgtatggg | ctgagggatg | gatgtcctgc | tgtttcctgc | agcttccagc | tcacacctcc | 360 |
| tctgtgtgtg | tgtgtggggg | ggggggttat | ttttatttcc | tgtgttcaat | ctgtggggct | 420 |
| gcaagccatt | taccacaact | actgtacatt | gttccttgct | cggcagtggt | gggaaacagc | 480 |
| cctttgcacc | ctctgcctac | acacttcctg | tcgccacggc | atgcaaatgt | tcctcctgct | 540 |
| tcctctcccg | gcagcctgca | cctctgctct | ggatccccg | ggctgcagga | attcgataaa | 600 |
| aaattaaata | ttgccgggcg | tggtccaccc | tttattccca | gcactcggga | ggaacagagg | 660 |
| caggcggatt | tctgagttcg | aggccagcct | ggtctacaga | gtgagtttca | ggcatccagg | 720 |
| gctacacaga | gaaaccctgc | ctggaaaaaa | aaaaagaaa | gaaaaattat | gtcatttccc | 780 |
| tttcacctcc | ttctcccctct | catctacttc | ctcctccaat | accctcccaa | tactttctca | 840 |
| aattcatggc | ctctggtttt | aattgtgata | ggtgtgtgta | tgtttatgca | cacacacaca | 900 |
| cacacacaca | cacacacaca | cacacacact | tatgatttca | gagctgacca | tctggtgttg | 960 |
| gatagctggt | tgggggcttc | tccctgggga | agaatgtttc | ccactgtcag | tgttgcttgg | 1020 |
| ctgctgcgct | ccttgtttag | ggttggagaa | tcccccctca | catttctaag | accaatctca | 1080 |
| gagcacactt | cctgtttctc | tggttcttac | agtcgttgtg | cccccaaccc | ccttctaaga | 1140 |
| tgttccctgc | gcctcgggtg | caggagctgg | gttgtcgata | gatccgctgg | agccgggcac | 1200 |
| cccaggatcc | acggtcctct | gcctctgaca | gggtgtggtt | ttctttctgt | atgcgtgcgt | 1260 |
| gcgcgtttgt | gagtgtgtca | gaggacatct | tggcaggagt | cggttctttc | cttgtaccat | 1320 |
| gtaggtacta | aggttcaagc | ttgggtcacc | agggcgtcac | taggtgcctt | gtatacagag | 1380 |
| tcatcttgtc | ttctgatttt | gccttatcac | tgaacttctg | accacggggc | tggcaaggtg | 1440 |
| gctcagagag | taaaaacccc | ttctgagcag | ccccggtgat | ctgagattga | ccccccccc | 1500 |
| cagcttccac | gcagaggtag | agaactgact | attgaagttc | tctgaccgtc | acaggcacgc | 1560 |
| gccacaccat | ccccgccatg | agactgagcc | tacagtttat | gcatctatta | tgctatgtat | 1620 |
| tccctcagca | ggggagccct | gtccacccat | gctccctgga | gtggacaggg | ctcgggtttg | 1680 |
| ccattctaat | tcagtcctaa | agaggaacca | agtaagtgat | caagcttatc | gatactgctg | 1740 |
| cccccgtgtg | gctaccttaa | gacactacaa | cagagtggga | ctcccaagac | gaaagttttt | 1800 |
| caggtttcag | gttctgcgac | ttcctaggac | cctgagagac | agatgtccac | tagggttatc | 1860 |
| tcttgacact | taaatttcct | cctggagtgg | aaatgagagc | gaatggggct | tcttgtggaa | 1920 |
| ggtatctgtt | ggggaacgag | ccttagctgt | gtgtgtaggc | agctgcctct | ttcacaacct | 1980 |
| gtccagcaca | agctggactg | gacatagact | ttctcccttg | aactaagtat | atagacttgt | 2040 |
| ctaatttgag | ggcaatagag | gtcaggggag | ggggacttct | tgggagtgga | gccgcagtgc | 2100 |

```
ctccccagcc ggctgctgtg aatgggtgtt accaccaaga cctgcaagcc ccacccaatg    2160
tgctctccgt ggccttcttt tctgcacctg tggttgggct cggtgtaac ggcccagcct    2220 acctcttctg ggcacgtggc ccggagagat cttatctcta actctgtatt tttaactcct    2280 cttttccagag gatgtggctt ctgcgggaga gcttcaaagg gggacctgtt tgcccatgtc   2340
agcagccgtg acgtcatgga agtgggaggc tgttcagacc caaacacctg gagggaagtg    2400
ggaaactttt tccatttcct gttctacttc tggctattga ttcactatct gaccagctta    2460
cccatttcag ggtgcagctc gag                                           2483
```

<210> SEQ ID NO 3
<211> LENGTH: 1362
<212> TYPE: DNA
<213> ORGANISM: Artificial Sequence
<220> FEATURE:
<223> OTHER INFORMATION: Entirely synthetic DNA sequence formed by
      standard recombinant DNA technology from four functional regions
      of TCR(alpha) LCR.

<400> SEQUENCE: 3

```
gcggccgctc tagaactagt gtgcttttgt ctcggggttg tgattttccc cttggactag     60
ccttggcggc aggcgtagct tgttgtgagt ttgtaccgtt tacaacagta caaactactt    120 tcagggtct tgagttcaaa tttgaaaatg caccataggc ttgctgtaga ctttagttag    180
cttgctctgt ggctctcagt tccatacgca cagagaggct aaccgtgggt tattcctcaa    240
ctagggaagg gccttccaca aggctccccg ggcggagggg ttggttttgc tgactcaggt    300
actgtatggg ctgagggatg gatgtcctgc tgtttcctgc agcttccagc tcacacctcc    360
tctgtgtgtg tgtgtggggg gggggttat ttttatttcc tgtgttcaat ctgtggggct    420
gcaagccatt taccacaact actgtacatt gttccttgct cggcagtggt gggaaacagc    480
cctttgcacc ctctgcctac acacttcctg tcgccacggc atgcaaatgt tcctcctgct    540
tcctctcccg gcagcctgca cctctgctct ggatccccg ggctgcagga attcgatatc     600
aagcttatcg atactgctgc cccgtgtgg ctaccttaag acactacaac agagtgggac    660
tcccaagacg aaagttttc aggtttcagg ttctgcgact tcctaggacc ctgagagaca    720
gatgtccact agggttatct cttgacactt aaatttcctc ctggagtgga aatgagagcg    780
aatgggcttt cttgtggaag gtatctgttg gggaacgagc cttagctgtg tgtgtaggca    840
gctgcctctt tcacaacctg tccagcacaa gctggactgg acatagactt tctcccttga    900
actaagtata tagacttgtc taatttgagg gcaatagagg tcaggggagg gggacttctt    960
gggagtggag ccgcagtgcc tccccagccg gctgctgtga atgggtgtta ccaccaagac   1020
ctgcaagccc acccaatgt gctctccgtg gccttctttt ctgcacctgt ggttgggctg    1080
cggtgtaacg gcccagccta cctcttctgg gcacgtggcc cggagagatc ttatctctaa    1140
ctctgtattt ttaactcctc ttttccagag atgtggcttc tgcgggagag cttcaaaggg   1200
ggacctgttt gcccatgtca gcagccgtga cgtcatggaa gtgggaggct gttcagaccc    1260
aaacacctgg agggaagtgg gaaacttttt ccatttcctg ttctacttct ggctattgat    1320
tcactatctg accagcttac ccatttcagg gtgcagctcg ag                      1362
```

<210> SEQ ID NO 4
<211> LENGTH: 29
<212> TYPE: DNA
<213> ORGANISM: Artificial Sequence
<220> FEATURE:

```
<223> OTHER INFORMATION: Synethic primer sequence

<400> SEQUENCE: 4
gacctgctcg agctgcaccc tgaaatggt                                29

<210> SEQ ID NO 5
<211> LENGTH: 29
<212> TYPE: DNA
<213> ORGANISM: Artificial Sequence
<220> FEATURE:
<223> OTHER INFORMATION: Synthetic primer sequence

<400> SEQUENCE: 5
cgagtcatcg atactgctgc ccccgtgtg                                29
```